United States Patent [19]
Nguyen et al.

[11] Patent Number: 6,006,123
[45] Date of Patent: Dec. 21, 1999

[54] ELECTRODE CATHETER SYSTEM AND METHODS FOR USING SAME

[75] Inventors: Tho Hoang Nguyen, Huntington Beach; Hosheng Tu, Tustin, both of Calif.

[73] Assignee: Irvine Biomedical, Inc., Irvine, Calif.

[21] Appl. No.: 09/169,107

[22] Filed: Oct. 9, 1998

Related U.S. Application Data

[63] Continuation-in-part of application No. 08/959,813, Oct. 29, 1997.

[51] Int. Cl.$^6$ .................................................. A61N 1/05
[52] U.S. Cl. ............................................ 600/374; 600/424
[58] Field of Search .................................. 600/372, 373, 600/374, 424; 604/95; 607/116, 119, 122

[56] References Cited

U.S. PATENT DOCUMENTS 5,755,760  5/1998  Maguire et al. ........................ 607/122
5,891,138  4/1999  Tu et al. ................................... 606/41
5,916,163  6/1999  Panescu et al. ......................... 600/424

*Primary Examiner*—George Manuel

[57] ABSTRACT

A method for positioning an electrode catheter system having safety means at its distal section within a heart chamber comprises percutaneously introducing the distal end of a catheter through an artery or vein to the heart chamber. Once the catheter tip is at the desired location, the connector of the handle at the proximal end is connected to an EKG monitor. And the electrical signal from the electrodes on the distal section can be transmitted to the exterior EKG monitor for cardiac mapping. Alternately, the radio frequency current can be supplied to one or more of the electrodes on the distal section once an intimate contact with a tissue is achieved using the catheter of this invention.

18 Claims, 4 Drawing Sheets

ELECTRODE CATHETER SYSTEM AND METHODS FOR USING SAME

This is a continuation-in-part of prior application Ser. No. 08/959,813 filed Oct. 29, 1997, now allowed.

FIELD OF THE INVENTION

The present invention generally relates to improved constructions for electrode catheter system. More particularly, this invention relates to apparatus and methods for diagnosing and treating cardiac arrhythmias via an electrode catheter system having a firm secured tip electrode at its distal end.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias that are frequently caused by the presence of an "arrhythmogenic region" or "accessory atrioventricular pathway" close to the inner surface of the chambers of a heart. The heart includes a number of normal pathways that are responsible for the propagation of electrical signals from upper to lower chamber necessary for performing normal function. The presence of arrhythmogenic region or accessory pathways can bypass or short circuit the normal pathways, potentially resulting in very rapid heart contractions, referred to here as tachycardias.

Cardiac mapping is used to locate aberrant electrical pathways and currents emanating within the heart. The aberrant pathways cause the contractions of the heart muscle to take on abnormal and life threatening dysrhythmias. Intracardiac mapping requires careful positioning of a plurality of catheters of multiple electrodes within the heart. For example, Webster, Jr. in U.S. Pat. No. 4,960,134 shows the general use of a catheter. It is important for a catheter to move into and out of the heart chamber freely without any obstruction or potential complications of component disengagement from the catheter shaft.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a clinician to be able to accurately steer the catheter to the region for ablation. Once at the region, it is important for a catheter to intimately contact the tissue to effectively control the emission of energy to ablate the tissue within the heart.

Regardless of the type of mapping means or ablation means used, the clinician is called upon to remotely move, rotate, push, pull, and manipulate the catheters in various ways. First, a catheter is inserted into a major vein or artery, usually in the neck or groin area. It is then guided into chambers of the heart by appropriate manipulation through the vein or artery. The distal section of a catheter must be manipulatable by a user from the proximal end of the catheter, so that the electrodes at the distal section can be positioned against the tissue at the desired location to assure that all aberrant electrical pathways are mapped and later ablated.

Development of prior electrode catheters has focused upon the requirements of electrical continuity and interference problems. However, the mechanical and safety considerations have been overlooked. In general, a conducting wire is soldered to the tip electrode or a band electrode. The electrode with a conducting wire is thereafter placed and secured onto the catheter shaft, mostly by gluing with an appropriate adhesive. The bonding force between a tip electrode and the catheter shaft is proportional to the contact surface area and is substantially maintained so long as the contact is intimate and intact. It has been reported that the tip electrode might sometimes disengage from the distal section of the catheter shaft. The frequency of tip electrode disengagement becomes more often as a result of thermal cycling to the catheter. This includes the cases of applying the RF energy to a tip electrode in ablation procedures or when the catheter is re-sterilized through high temperature cycles. In one instance, an electrode catheter can be made of PebaxTm material, which is polyether/amide block copolymer (supplied by Elf Atochem North America, Inc., Philadelphia, Pa.). Its coefficient of linear thermal expansion is reported as $220 \times 10^{-6}$ inch/inch/° C. For a catheter to endure an ablation temperature of up to 90° C., the linear thermal expansion from the room temperature of 25° C. is calculated as 1.4%. In other words, the plastic portion may expand by a factor of 1.4% when its temperature is increased from 25° C. to 90° C. Repetitive cycles of thermal expansion and contraction may lead to eventual failure of the bonding force between the catheter shaft and the tip electrode.

The electrode is generally prone to separating from its main catheter shaft body because of repetitive thermal cycling, resulting in separation of the catheter shaft from the stem of a tip electrode. The tip electrode might inadvertently be separated from the catheter shaft and be left behind in a patient's heart or in a circulation system, causing undesired health hazard.

The prior catheter development has overlooked the important need to provide a safe catheter system having safety means in association with the required bonding force. It is an objective of this invention to provide needed safety means for the electrophysiology cardiovascular catheter system having a tip electrode.

SUMMARY OF THE INVENTION

It is an object of the present invention to provide an improved electrode catheter system that can be used in mapping and ablating an arrhythmogenic region. It is another object of the present invention to provide safety means to the electrode catheter system so that the integrity of the catheter is maintained throughout the thermal cycling of ablation procedures or sterilization process.

In one embodiment, an electrode catheter system of this invention comprises a catheter shaft having a distal section, a distal end, a proximal end, and at least one lumen extending therebetween; a handle attached to the proximal end of the shaft, wherein the handle has a proximal end and a distal end and wherein a connector is secured to the proximal end of the handle; a plurality of electrodes disposed at the distal section, wherein a tip electrode is secured at the distal end of the catheter; and an appropriate ring with its inner diameter matching the outer diameter of the catheter shaft being secured on the outside of the very distal end of the catheter shaft to restrict the distal end from thermal expansion during thermal cycling. Said ring which may function as a first band electrode is to restrict the distal end of the catheter shaft from thermal expansion through the thermal cycling. In another embodiment, the ring that is secured on the catheter shaft with addition of adhesives or glues, is a band electrode, an inactive end-ring, a mesh, or a spiral element at the very distal end of the catheter shaft. By using said first band electrode or ring as safety means to restrict the distal end of the catheter shaft from thermal expansion, the tip electrode is firmly secured on the catheter shaft. The catheter shaft is therefore firmly sandwiched between two coaxial metal means, i.e., the inner surface of the band electrode and the outer surface of the stem of said tip electrode.

In another embodiment, the first band electrode that is a ring type, becomes an integral part of the "captive" tip electrode. Therefore, the very distal portion of the catheter shaft is sandwiched within the space between said ring portion and the stem portion of said captive tip electrode. By using the space between the ring and stem portions of the captive electrode as safety means to restrict the distal end of the catheter shaft from thermal expansion and contraction, the tip electrode is firmly secured on the catheter shaft.

In still another embodiment, a catheter system of this invention comprises a catheter shaft having a distal section, a distal end, a proximal end, and at least one lumen extending therebetween; a handle attached to the proximal end of the shaft, wherein the handle has a proximal end and a distal end and wherein a connector is secured to the proximal end of the handle; a plurality of electrodes disposed at the distal section, wherein a tip electrode is secured at the distal end of the catheter; a first band electrode secured at the distal end of said catheter shaft; and an extended stem of the tip electrode having at least one open slot in the axial direction on the stem being provided. In an alternate embodiment, the extended stem of the tip electrode is a flexible stem. The open slot on the stem is to provide adequate clearance for at least a conducting wire to enter from the adjacent band electrode into the lumen. The extended flexible stem may consist of the material such as the braided metal mesh in a spiral-convoluted form. The length of the extended stem may be equal to or longer than the length of the tip electrode. In a preferred embodiment, the proximal end of the stem having at least one open slot in a catheter system extends proximally beyond the distal edge of the first band electrode.

The distal section of the electrode catheter system of this invention can be either a fixed curve type or a deflectable curve type. In an exemplary embodiment, the means for deflecting the distal section of a steerable catheter comprises at least two pull wires along with a support wire. Said pull wires are attached to radially offset locations at the distal end of the deflectable section of the catheter shaft whereas at least a support wire radially in-between the pull wires, and means at the proximal end of the shaft for selectively applying tension to the pull wires to cause deflection of the deflectable portion. In certain cases, the function of a support wire can be substituted by a spring coil that is stationary at its proximal end with respect to the shaft. The catheter system further comprises a steering mechanism at the handle, wherein said steering mechanism provides a plurality of deflectable curves on the tip section of the catheter assembly. The incorporation of the steering mechanism in a catheter is well known to those who are skilled in the art.

The means for selectively applying tension comprises a steering mechanism in the handle, and means for applying torque to the core wire comprises a rotatable ring or push-pull button disposed on the handle, the ring or button being coupled to the proximal end of the core wire. A variety of other tensions applying mechanisms, such as joysticks, may also be employed.

There is at least one temperature sensor associated with at least one selected electrode. The temperature sensor is attached to the electrode at the same side of tissue contact site. The multiple temperature sensors are important to independently measure and monitor the true tissue contact temperature upon contacting each and every ablation electrode during RF energy delivery. During multiple electrodes ablation, the tissue contact temperatures are not the same depending on such variables as the RF energy time, the intimacy of tissue-electrode contact, the location of the temperature sensor on the electrode, and tissue thermal conductivity parameters. Due to continuous heart movement, a good tissue contact becomes significant in affecting the temperature readings. The size of lesions is a function of RF energy, time, tissue contact characteristics, and temperature control.

In other embodiment, an ablation catheter further comprises a closed-loop temperature control mechanism for each selected electrode having at least a temperature sensor. An ablation catheter of this invention further comprises RF energy, microwave energy, or ultrasound energy delivery. To better control the desired lesion, more energy may be needed when the measured tissue contact temperature is relatively low. On the other hand, less energy is needed when a relatively high tissue contact temperature is measured. In still another embodiment, an ablation catheter further comprises a programmed temperature control mechanism for independently controlling each electrode ablation of the catheter system according to the software program prepared by the operator.

Signal conducting electrodes are placed on the distal section while their insulated conducting wires are passed through the shaft lumen to the contact pins of a connector secured at the proximal end of the handle. The main purpose of the conducting wires is to transmit the electric signal and to provide means for RF current delivery. The safety restricting end-ring and/or extended flexible stem on the tip electrode reinforce the gluing strength of the tip electrode.

A method for positioning an electrode catheter system having safety means at its distal section within a heart chamber comprises percutaneously introducing the distal end of a catheter through an artery or vein to the heart chamber. Once the catheter tip is at the desired location, the handle at the proximal end is connected to an EKG monitor. And the electrical signal from the electrodes on the distal section can be transmitted to the exterior EKG monitor for cardiac mapping. Alternately, the radio frequency current can be supplied to one or more of the electrodes on the distal section once an intimate contact with the tissue is achieved using the catheter of this invention.

The method and apparatus of the present invention have several significant safety advantages over known electrode catheters. In particular, the restricting ring associated with or on the tip electrode is to maintain the integrity of the tip electrode of the catheter system from potential complications of undesired components disengagement.

BRIEF DESCRIPTION OF THE DRAWINGS

Additional objects and features of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
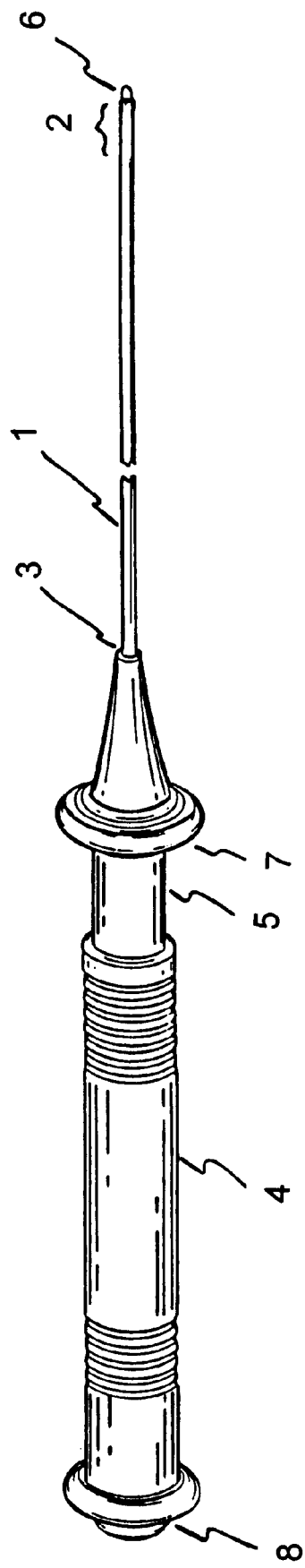
FIG. 1 is an overall view of the electrode catheter system having a restricting ring and a secured tip electrode constructed in accordance with the principles of the present invention.

FIG. 1 shows an electrode catheter system constructed in accordance with the principles of the present invention comprising: a catheter shaft 1 having a distal tip section 2, a distal end 6, a proximal end 3 and at least a lumen extending therebetween. A handle 4 is attached to the proximal end 3 of the catheter shaft 1. The tip section 2 may be a fixed curve type or deflectable type by optionally employing a steering mechanism 5 at the handle 4. A push-pull plunger 7, in the case of a steerable catheter system, is employed to deflect the tip section 2 of the catheter shaft 1. A connector 8 is secured at the proximal end of the handle 4. At least one electrode available for electrophysiology use and a restricting ring is disposed at the very distal end of the tip section 2.

Figure 2:
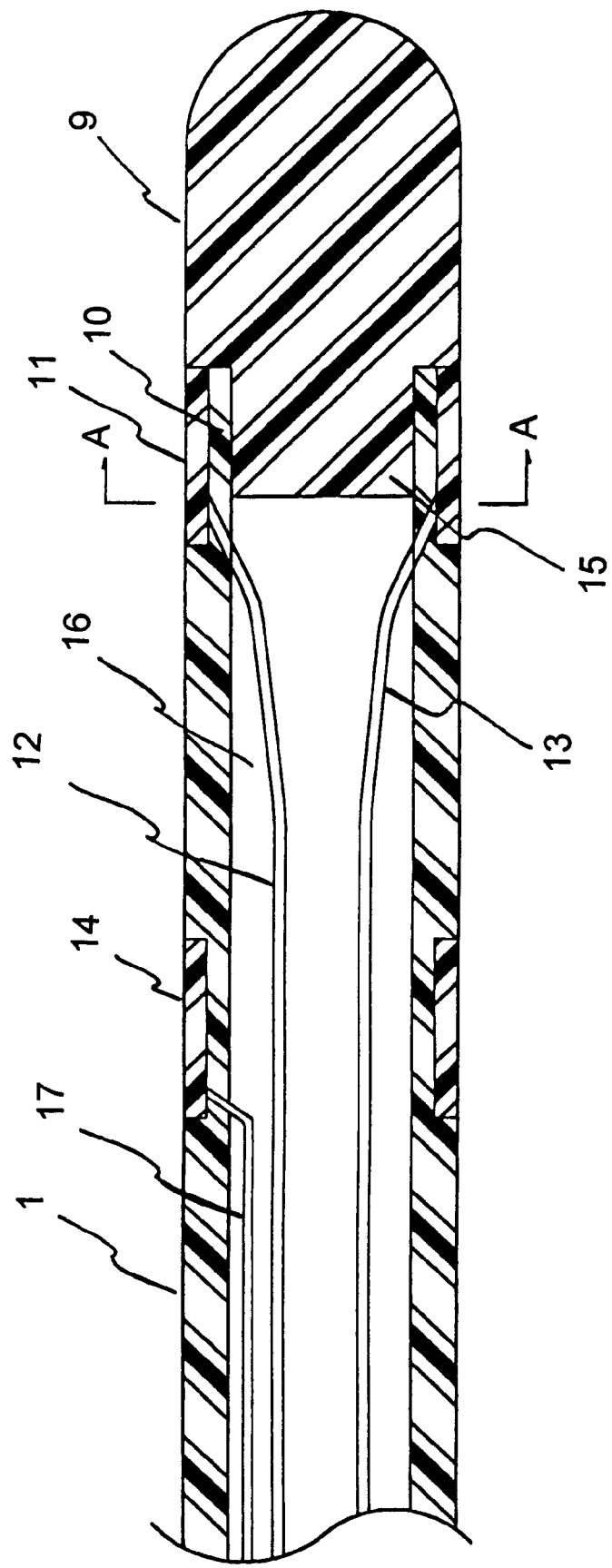
FIG. 2 is a close-up view of the distal section of the electrode catheter system of FIG. 1.

FIG. 2 shows a perspective view of the distal section of an electrode catheter system with safety end-ring as safety means of FIG. 1. The tip electrode 9 is attached to the catheter shaft 1 using either epoxy or glue. The outer diameter of the very distal end 10 of the catheter shaft 1 is reduced so that a first band electrode 11 is secured onto it. In one embodiment, said first band electrode is a ring which is secured onto the distal end 10 with assistance of adhesive or glues. In another embodiment, the first band electrode 11 has a conducting wire 12 for measuring the electrical signal and delivering the RF energy. The conducting wire 12 from the band electrode 11 passes through the lumen 16 of the catheter shaft 1 and is secured to the contact pin of a connector 8 at the proximal end of the handle 4. Similarly another conducting wire 17 is attached to the other band electrode 14 for measuring the electrical signal and/or delivering the RF energy. In a further embodiment, a temperature sensor and conducting means 13 is connected to said band electrode 11. Adhesive and/or glue may be added when securing the stem 15 of said tip electrode 9 into the distal opening of the shaft 1. By incorporating said safety means of a restricting first band electrode 11 or end-ring at the very distal end of the catheter shaft 1, said tip electrode 9 is secured onto the tip section of the catheter system. At least one additional band electrode 14 can be added to the electrode catheter system of this invention. In a further embodiment, the tip electrode is a non-active cap.

Figure 3:
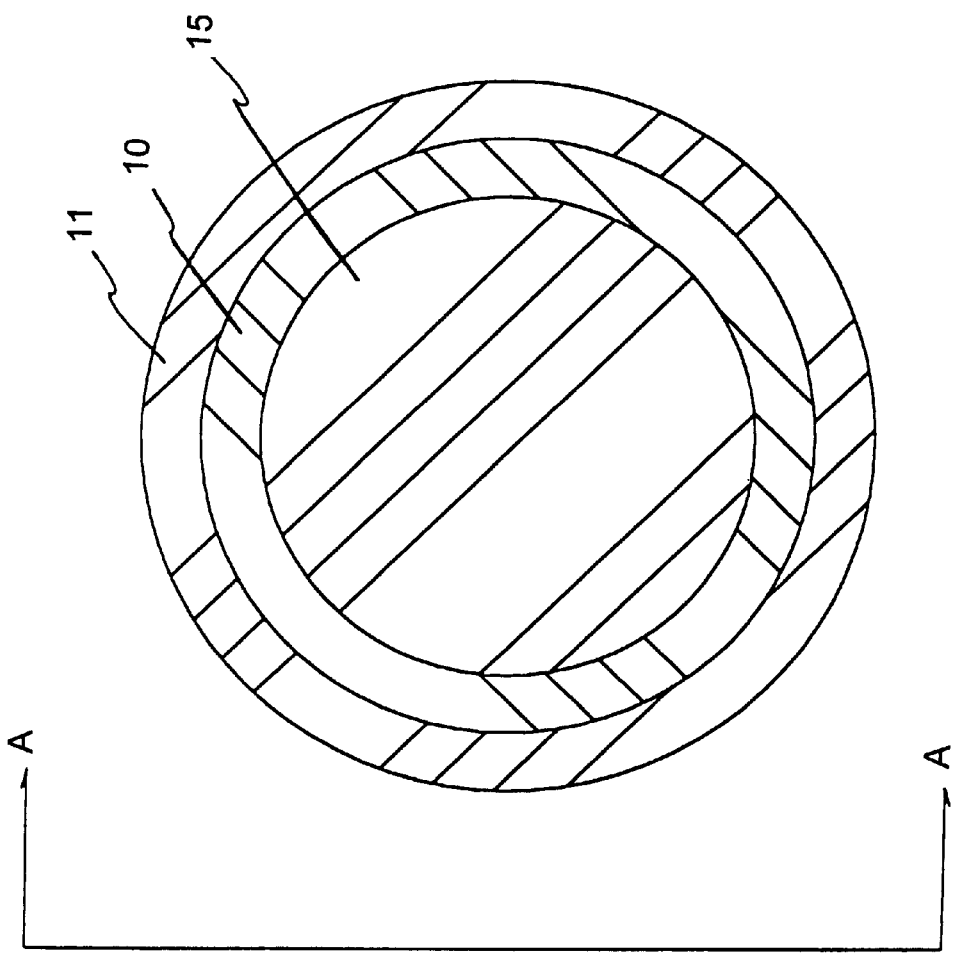
FIG. 3 is a cross-sectional view of the distal section of the electrode catheter system of FIG. 2.

FIG. 3 shows the cross-sectional view of the tip section of FIG. 2. The reduced distal portion 10 of the catheter shaft 1 is sandwiched firmly between the end-ring or first band electrode 11 and the stem 15 of the tip electrode 9.

Figure 4:
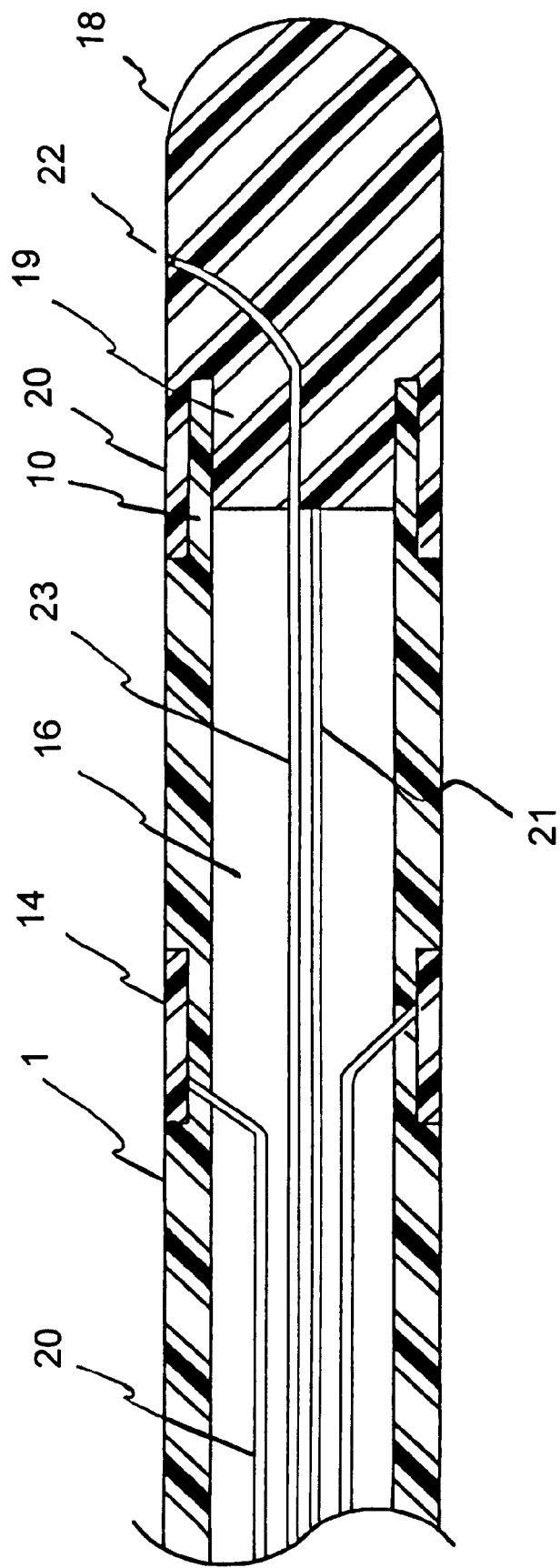
FIG. 4 is an alternate view of the distal section of the electrode catheter system.

FIG. 4 shows an alternate view of the distal section of an electrode catheter system of this invention. The "captive" tip electrode 18 which has a stem 19 and has an outer ring 20 is to be fitted into the reduced distal end 10 of the catheter shaft 1. Adhesive and/or glue may be applied during insertion of the stem 19 of said tip electrode. At least a band electrode 14 is secured at the distal tip section 2 of the catheter system. A conducting wire 20 from the band electrode 14 passes through the catheter shaft 1 through a small opening on the catheter shaft and enters into the lumen 16 which is thereafter secured to one contact pin of the connector 8 at the proximal end of the handle 4. Similarly, another conducting wire 21 from the tip electrode 18 is also secured to one pin of the connector 8. A temperature-measuring sensor 22 is secured at the tissue contact side of the tip electrode 18. The temperature sensing wire 23 is connected to an external measuring monitor and/or to a temperature control mechanism. Similarly, another temperature sensing means is provided to other electrodes for ablation monitoring and temperature control purpose.

In another embodiment, the steerable electrode catheter of the present invention comprises a handle and a catheter shaft, wherein a tip electrode and a first band electrode are disposed at the very distal end of the catheter shaft. The steerable catheter has a push-pull plunger as a steering mechanism to deflect the tip of the catheter to a desired curve type.

The material of electrodes may be selected from the group of platinum, iridium, silver, gold, Nitinol, or stainless steel. The spacing between the electrodes is in the range of 1 mm to 10 mm, preferably 2 to 5 mm. The length of the stem is in the range of 2 mm to 20 mm, preferably 2 to 10 mm.

From the foregoing, it should now be appreciated that an improved electrode catheter system has been disclosed herein comprised of safety means to render a catheter less prone to disintegration. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A method for operating an electrode catheter system within a heart chamber, the electrode catheter system comprising a catheter shaft having a distal section, a shaft distal end, a shaft proximal end, and at least one lumen extending therebetween; a handle attached to the shaft proximal end of the catheter shaft, wherein the handle has a proximal end and a distal end and wherein a connector is secured to the proximal end of the handle; a plurality of electrodes disposed at the distal section, wherein a tip electrode is secured at the shaft distal end of the catheter; and an appropriate ring with its inner diameter matching the outer diameter of the catheter shaft being secured on the outside of the shaft distal end of the catheter shaft to restrict the shaft distal end from thermal expansion during thermal cycling;

the method comprising the steps of:
 (a) percutaneously introducing the shaft distal end of a catheter through an artery or vein to a heart chamber;
 (b) once the catheter distal section is positioned, the connector at the proximal end of the handle is connected to an EKG monitor, wherein an electrical signal from the plurality of electrodes at the distal section is transmitted to an exterior EKG monitor for cardiac mapping.

2. The method for operating an electrode catheter system within a heart chamber as in claim 1, the electrode catheter system further comprising a radiofrequency current generator, wherein the radiofrequency current is delivered to the plurality of electrodes.

3. The method for operating an electrode catheter system within a heart chamber as in claim 1, wherein said tip electrode is an inactive cap.

4. The method for operating an electrode catheter system within a heart chamber as in claim 1, the electrode catheter system further comprising a steering mechanism at the handle for the electrode catheter system.

5. The method for operating an electrode catheter system within a heart chamber as in claim 4, wherein said steering mechanism provides a plurality of deflectable curves on the distal section of the electrode catheter system.

6. The method for operating an electrode catheter system within a heart chamber as in claim 1, the electrode catheter system further comprising a closed-loop temperature control mechanism for the electrode having at least one temperature sensor.

7. A method for operating an electrode catheter system within a heart chamber, the electrode catheter system comprising a catheter shaft having a distal section, a distal end, a proximal end, and at least one lumen extending therebetween; a handle attached to the proximal end of the catheter shaft, wherein the handle has a proximal end and a distal end and wherein a connector is secured to the proximal end of the handle; a plurality of electrodes disposed at the distal section, wherein a "captive" tip electrode of said electrodes is secured at the distal end of the catheter shaft and said tip electrode is comprised of a ring portion, a stem portion and a cylindrical space therebetween; and a reduced distal end of the catheter shaft being sandwiched firmly into said space of the tip electrode to restrict said distal end from thermal expansion during thermal cycling;

the method comprising the steps of:
(a) percutaneously introducing the shaft distal end of a catheter through an artery or vein to a heart chamber;
(b) once the catheter distal section is positioned, the connector at the proximal end of the handle is connected to an EKG monitor, wherein an electrical signal from the plurality of electrodes at the distal section can be transmitted to an exterior EKG monitor for cardiac mapping.

8. The method for operating an electrode catheter system within a heart chamber as in claim 7, the electrode catheter system further comprising a radiofrequency current generator, wherein the radiofrequency current is delivered to the plurality of electrodes.

9. The method for operating an electrode catheter system within a heart chamber as in claim 7, wherein said tip electrode is an inactive cap.

10. The method for operating an electrode catheter system within a heart chamber as in claim 7, the electrode catheter system further comprising securing said reduced distal end of the catheter shaft sandwiched firmly into said space of the tip electrode with addition of adhesives or glues.

11. The method for operating an electrode catheter system within a heart chamber as in claim 7, the electrode catheter system further comprising a steering mechanism at the handle for the electrode catheter system.

12. A method for operating an electrode catheter system within a heart chamber, the electrode catheter system comprising a catheter shaft having a distal section, a distal end, a proximal end, and at least one lumen extending therebetween; a handle attached to the proximal end of the catheter shaft, wherein the handle has a proximal end and a distal end and wherein a connector is secured to the proximal end of the handle; a plurality of electrodes disposed at the distal section, wherein a tip electrode is secured at the distal end of the catheter; an extended stem of the tip electrode having at least one open slot in the axial direction on the stem being provided; and an appropriate ring with its inner diameter matching the outer diameter of the catheter shaft being secured on the outside of very distal end of the catheter shaft to restrict the distal end from thermal expansion during thermal cycling;

the method comprising the steps of
(a) percutaneously introducing the shaft distal end of a catheter through an artery or vein to a heart chamber;
(b) once the catheter distal section is positioned, the connector at the proximal end of the handle is connected to an EKG monitor, wherein an electrical signal from the plurality of electrodes at the distal section can be transmitted to an exterior EKG monitor for cardiac mapping.

13. The method for operating an electrode catheter system within a heart chamber as in claim 12, the electrode catheter system farther comprising a radiofrequency current generator, wherein the radiofrequency current is delivered to the plurality of electrodes.

14. The method for operating an electrode catheter system within a heart chamber as in claim 12, wherein said tip electrode is an inactive cap.

15. The method for operating an electrode catheter system within a heart chamber as in claim 12, the electrode catheter system further comprising securing said reduced distal end of the catheter shaft sandwiched firmly into said space of the tip electrode with addition of adhesives or glues.

16. The method for operating an electrode catheter system within a heart chamber as in claim 12, the electrode catheter system further comprising a steering mechanism at the handle for the electrode catheter system.

17. The method for operating an electrode catheter system within a heart chamber as in claim 12, wherein the extended stem of the tip electrode is a flexible stem.

18. The method for operating an electrode catheter system within a heart chamber as in claim 17, wherein the flexible stem is consisted of a braided metal mesh in a spiral-convoluted form.

* * * * *